United States Patent
Sherman et al.

[19]

[11] Patent Number: 5,976,135
[45] Date of Patent: Nov. 2, 1999

[54] LATERAL CONNECTOR ASSEMBLY

[75] Inventors: Michael C. Sherman, Memphis; Eddie Ray, III, Cordova; Troy Drewry, Memphis, all of Tenn.; David Shapiro, Highland Park, Ill.

[73] Assignee: SDGI Holdings, Inc., Wilmington, Del.

[21] Appl. No.: 08/992,975

[22] Filed: Dec. 18, 1997

[51] Int. Cl.⁶ .................................................. A61B 17/70
[52] U.S. Cl. ............................................................ 606/61
[58] Field of Search ............................. 606/59, 61, 62, 606/63, 64, 72, 73, 60, 86

[56] References Cited

U.S. PATENT DOCUMENTS

| | | | |
|---|---|---|---|
| 5,127,912 | 7/1992 | Ray et al. | 606/61 |
| 5,129,900 | 7/1992 | Asher et al. | 606/61 |
| 5,147,360 | 9/1992 | Dubousset | 606/61 |
| 5,246,442 | 9/1993 | Ashman et al. | 606/61 |
| 5,261,909 | 11/1993 | Sutterlin et al. | 606/61 |
| 5,282,801 | 2/1994 | Sherman | 606/61 |
| 5,312,404 | 5/1994 | Asher et al. | 606/61 |
| 5,344,422 | 9/1994 | Frigg | 606/61 |
| 5,364,399 | 11/1994 | Lowery et al. | 606/69 |
| 5,403,315 | 4/1995 | Ashman | 606/61 |
| 5,403,316 | 4/1995 | Ashman | 606/61 |
| 5,437,669 | 8/1995 | Yuan et al. | 606/61 |
| 5,437,670 | 8/1995 | Sherman et al. | 606/61 |
| 5,474,551 | 12/1995 | Finn et al. | 606/61 |
| 5,476,463 | 12/1995 | Boachie-Adjei et al. | 606/61 |
| 5,487,744 | 1/1996 | Howland | 606/61 |
| 5,498,263 | 3/1996 | DiNello et al. | 606/61 |
| 5,499,983 | 3/1996 | Hughes | 606/61 |
| 5,527,314 | 6/1996 | Brumfield et al. | 606/61 |
| 5,582,612 | 12/1996 | Lin | 606/61 |
| 5,591,165 | 1/1997 | Jackson | 606/61 |
| 5,607,425 | 3/1997 | Rogozinski | 606/61 |
| 5,688,272 | 11/1997 | Montague et al. | 606/61 |
| 5,693,053 | 12/1997 | Estes | 606/61 |

FOREIGN PATENT DOCUMENTS

| | | |
|---|---|---|
| 0 553 424 A1 | 8/1993 | European Pat. Off. . |
| 2 656 214-A1 | 6/1991 | France . |

OTHER PUBLICATIONS

TSRH® *Spinal System*, Page from Brochure featuring TACOMA® Plates and Screws, A–108.
GDLH® *Posterior Spinal System*, Page from Brochure featuring Rods and Connectors, A–53.

*Primary Examiner*—Michael Buiz
*Assistant Examiner*—Vikki Trinh
*Attorney, Agent, or Firm*—Woodard, Emhardt, Naughton, Moriarty & McNett

[57] ABSTRACT

A lateral connector assembly for connecting a bone engaging fastener to an elongated member, such as a spinal rod includes a lateral connector having an elongated opening for receiving a portion of the bone engaging fastener therethrough. The lateral connector includes a plate portion and an integral yoke portion, which yoke portion is attached to the elongated member by way of a clamp. The lateral connector assembly can include variable angle means between the clamp and the yoke portion of the lateral connector that permits rotation of the lateral connector about an axis projecting outward from the spinal rod. The plate portion and the yoke portion of the lateral connector are oriented at non-perpendicular angles, preferably an angle greater than 100 degrees. In a further embodiment the plate portion of the lateral connector is curved so that as the bone engaging fastener slides along the elongated opening, it assumes variable angular orientations relative to the lateral connector assembly and the elongated rod.

21 Claims, 2 Drawing Sheets

LATERAL CONNECTOR ASSEMBLY

BACKGROUND OF THE INVENTION

The present invention generally concerns spinal fixation systems, such as systems for use in the fixation of the spine for the treatment of various spinal deformities. Specifically, the present invention contemplates a lateral connector assembly for interconnecting an elongated member, such as a plate or a rod, with a bone engaging fastener, such as a hook, screw or bolt.

The treatment of spinal deformities and injuries has evolved significantly over the last 30 years. Spinal deformities, such as scoliosis and kyphosis, as well as fractures, spondylolisthesis, and other medical indications have been treated using a system of relatively rigid elongated members spanning the vertebral column. In one type of system, the elongated members constitute a plate that has a number of openings or slots through which bone bolts or bone screws extend. The bone engaging fasteners are threaded into different aspects of the vertebra to achieve fixation of the elongated plate. One system of this type is the DYNA-LOK® Spinal System provided by Sofamor Danek Group, Inc. of Memphis, Tenn.

In another approach, the system includes a generally rigid spinal rod sized to span along the length of the vertebral column. In this system, a variety of bone engaging fasteners are connected to the spinal rod by way of a clamp. In some systems, such as the CD™, CD HORIZON™ and LIBERTY™ spine systems marketed by Sofamor Danek, the fixation elements are threaded directly onto the spinal rod and held in place by a system of set screws. In this approach, the bone engaging fastener is situated directly in line with or beneath the spinal rod. The LIBERTY™ System also includes the STAR™ connector which is threaded onto the rod and provides for lateral connection of the same bone engaging fasteners.

In another type of rod-based spinal system, the bone engaging fasteners are connected laterally to the spinal rod. Two such systems are the TSRH® and the GDLH® spinal systems provided by Sofamor Danek. In these two systems, arrangements of eyebolts or T-bolts are threaded onto the rod and provide an interface to the bone engaging fastener, such as a hook or a screw. The TSRH® Spinal System includes bone screws, with one type having a central post that is engaged directly to the spinal rod, and another type providing variable angle capability, such as the TSRH® variable angle bone screw as shown and described in U.S. Pat. No. 5,261,909, to Sutterlin et al. As disclosed in the '909 Patent, which disclosure is incorporated herein by reference, the variable angle bone screw can achieve variable angular positions in a plane adjacent and perpendicular to the radius of the spinal rod. The TSRH® variable angle screw thus provides an additional degree of freedom for attaching the bone engaging fastener to the spinal rod over the fastener having a central post.

It is of course known in the field of spinal instrumentation that the fixation system must adapt to the spinal anatomy, both the original anatomy and the desired corrected anatomy. Movement or manipulation of the components of the system in different degrees of freedom has become essential to achieving proper correction and fixation. Consequently, the TSRH® Spinal System is provided with T-bolts for engaging the variable angle screws that provide an additional degree of freedom by laterally displacing the screw from the rod at predetermined distances. Lateral offset plates are also included which can be moved to adjustable lateral distances from the spinal rod to connect to the bone engaging fastener.

In the other type of rod-based system, as illustrated by the GDLH® posterior spinal system, bone bolts can be provided for fixation to the vertebrae. The bone bolts include a lower portion threaded for engagement in the vertebral bone, and an upper machine threaded portion. The GDLH® System includes various rod/bolt connectors for attaching the bolt to a spinal rod. In one type of GDLH® rod/bolt connector, the connector includes a single hole through which the machine threaded portion of the bone engaging fastener extends. A nut is threaded onto the machine threads to clamp the bone bolt to the connector. In this type of rod/bolt connector, the bone bolt is held at a fixed lateral position relative to the spinal rod. In another type of GDLH® rod/bolt connector, the connector includes an elongated opening or slot which allows relative lateral movement of the bone bolt with respect to both the connector and the spinal rod. With this GDLH® rod/bolt connector, the bone bolt can be engaged to the rod at variable lateral distances from the rod. Again, this feature allows the surgeon to accommodate variations in the spinal anatomy with respect to the placement of the spinal rod.

In the implantation of any spinal instrumentation, one goal of the surgeon is to minimize the intrusion into the patient, whether by the amount of implants that must be used or by the length of time required to fix the implants within the patient. In the early days of spinal fixation, the surgeon was limited in the locations and manner in which the bone engaging fasteners could be fixed to the vertebrae, and ultimately attached to an elongated member, such as a plate or a rod. As the spinal fixation systems became more elegant, the surgeon was been provided with additional degrees of freedom for movement and positioning of the bone engaging fasteners and the elongated members, either individually or with respect to each other. The use of lateral connectors between the bone engaging fastener and a spinal rod, for instance, has provided an additional degree for freedom to the surgeon. Adding the elongated slot for engagement to a bone bolt, such as in the GDLH® Spinal System, or providing T-bolts of varying lengths to engage the variable angle bone screw of the TSRH® Spinal System, adds a further degree of freedom. With these components providing lateral variability of the connection between the fastener and the rod, the surgeon need not bend the rod laterally to meet the position of the bone engaging fastener. For example, in some indications, a bone bolt is threaded into the pedicle of the vertebra. During the correction process, the spinal rod may not be directly aligned over or adjacent to the top of the bone bolt. In prior less sophisticated systems, the surgeon was required to bend the rod laterally so that the rod could be positioned directly adjacent the bone engaging fastener for connection between the two components. The addition of the lateral variability provided by the GDLH® and TSRH® components discussed above eliminates this bending requirement.

While this lateral adjustment feature has proven to very beneficial to spinal surgeons, additional degrees of freedom can still greatly improve the surgeon's task in quickly and efficiently instrumenting a patient's spine. The starting point of any spinal surgery is the spine itself, and more specifically the position and orientation of each of the vertebrae to be instrumented. Each vertebra has only a few "engagement points" onto which can be affixed a bone engaging fastener, such as a hook, screw or bolt. If that engagement point of the vertebra does not match the location of the connector for fixing the fastener to the elongated member, the surgeon must either manipulate the vertebra, or manipulate and/or bend the elongated member. In order to avoid this mechanical manipulation, it is desirable to provide the surgeon with additional degrees of freedom to more easily accommodate all possible orientations of a bone engaging fastener when it is engaged to a vertebra.

Consequently, there remains a need for providing a means for connecting a bone engaging fastener with an elongated member not only at variable lateral positions, as provided in some prior systems, but also at additional degrees of freedom relative to the rod. This need specifically encompasses variable angular orientations between the bone engaging fastener and the elongated member to which the fastener is to be connected.

SUMMARY OF THE INVENTION

In view of this need, the present invention provides a lateral connector assembly for connecting a bone engaging fastener to an elongated member. In a preferred embodiment, the elongated member is a spinal rod. The lateral connector assembly includes a lateral connector having an elongated opening for receiving a portion of the bone engaging fastener therethrough. The lateral connector includes a plate portion and an integral yoke portion, which yoke portion is attached to the elongated member by way of a clamp.

In certain embodiments, the lateral connector assembly includes variable angle means between the clamp and the yoke portion of the lateral connector. The variable angle means permits rotation of the lateral connector about an axis projecting outward from the spinal rod. In accordance with specific embodiments, the variable angle means includes interdigitating splines between the clamp and the yoke portion of the lateral connector.

In another aspect of the invention, the lateral connector assembly contemplates the plate portion and the yoke portion of the lateral connector being oriented at non-perpendicular angles. In other words, in this aspect of the invention, planes containing the plate portion and yoke portion define an angle of greater than 90 degrees, and most preferably greater than 100 degrees.

In yet another aspect of the invention, one embodiment of a lateral connector assembly includes a plate portion of the lateral connector that is curved. More specifically, the elongated opening or slot defined in the plate portion of the lateral connector is curved so that as the bone engaging fastener slides along the elongated opening, it assumes variable angular orientations relative to the lateral connector assembly and the elongated rod.

One object of the present invention is to provide a lateral connector assembly for connecting a bone engaging fastener, such as a hook, screw or bolt, to an elongated member, such as a spinal rod, extending along the length of the spine. One important object and benefit achieved by the present invention is that the lateral connector assembly permits multiple degrees of freedom of relative orientation between the fastener and the spinal rod.

A further object is accomplished by features of the invention that allow the surgeon to connect a spinal rod to a fastener engaged within a vertebra, virtually without regard to the particular orientation of the fastener relative to the rod. An additional benefit of the present invention is that the lateral connector assembly is easily manipulated to provide the link between the bone engaging fastener and the spinal rod and to provide for solid fixation of the components to each other. Other objects and benefits of the present invention can be discerned from the following written description and accompanying figures.

DESCRIPTION OF THE PREFERRED EMBODIMENTS

For the purpose of promoting an understanding of the principles of the invention, reference will now be made to preferred embodiments thereof and specific language will be used to describe the same. It will nevertheless be understood that no limitation of the scope of the invention is thereby intended, such alterations and further modifications in the invention, and such further applications of the principles of the invention as described therein being contemplated as would normally occur to one skilled in the art to which the invention relates.

Figure 1:
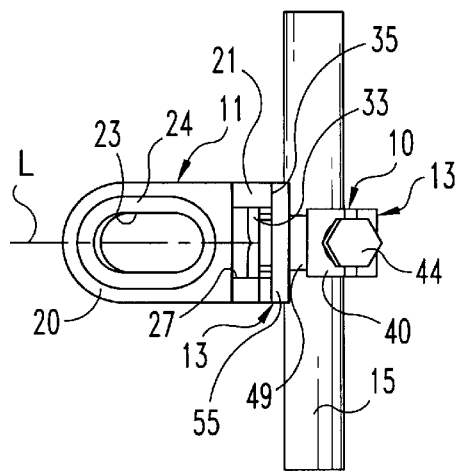
FIG. 1 is a top elevational view of a lateral connector assembly engaged to an elongated spinal rod according to one embodiment of the present invention.

Referring to FIG. 1, a portion of a spinal fixation assembly is depicted in which a lateral connector assembly 10 according to the present invention is engaged to an elongated member, such as a spinal rod 15. The lateral connector assembly 10 generally includes a lateral connector 11, a clamp 12 and variable angle means 13 between the clamp and the lateral connector. The rod 15 is configured to span at least two vertebrae. In the preferred embodiment, the elongated member is a rod, although the present invention contemplates substituting an elongated plate with appropriate modifications to the clamp 12.

The lateral connector 11 is used to connect a bone engaging fastener to the rod 15. In this respect, the lateral connector 11 is similar to the rod/bolt connectors of the GDLH® Spinal System, such as Sofamor Danek part nos. 855-038 and 855-039. As with these GDLH® components, the lateral connector 11 accepts a portion of a bone engaging fastener, which fastener can be separately clamped to the lateral connector to fix its position relative to the rod 15 when the lateral connector assembly 10 is engaged to the rod. In the preferred embodiment, the lateral connector 11 includes a plate portion 20 and an integral yoke portion 21. The yoke portion defines a pair of tool recesses 22 on its opposite lateral sides to permit gripping of the lateral connector 11 by an appropriate tool. In this respect, the tool recesses 22 are similar in configuration to the tool recesses in the TSRH® variable angle screw, such as the screw sold by Sofamor Danek under catalog no. 828-775, which is configured to be grasped by a hook holder provided as catalog no. 808-180. As with the aforementioned TSRH® components, the lateral connector 11 can be manually manipulated by the surgeon using the separate insertion instrument, or hook holder, to position the lateral connector adjacent the spine and preferably over a bone engaging fastener already in place on a given vertebra.

The lateral connector 11 further includes an elongated opening 23, or slot, defined within the plate portion 20. The elongated opening 23 extends through the plate portion from the top surface to the bottom surface. In the preferred embodiment, the opening 23 includes a countersink 24 around its perimeter at both the top and bottom surfaces. The countersink is preferably spherical to mate with corresponding spherical features on a bone engaging fastener. This countersink feature is similar to the countersink in the GDLH® rod/bolt connector, and is provided to permit some degree of angulation of the bone engaging fastener with respect to the plate portion 20 of the lateral connector 11.

The yoke portion 21 of the lateral connector 11 defines a hub opening 27 between two arms of the yoke. In accordance with the preferred embodiment, the hub opening 27 has an open end 28 and a recess 29 at the opposite end of the hub opening. The open end 28 permits top loading insertion of a portion of the clamp 12. The recess 29 defines a mounting surface offset below the surface of the yoke portion 21. In a specific embodiment, the recess 29 is circular in configuration and has a depth that is calibrated with respect to the clamp 12, as described more fully herein.

Figure 3:
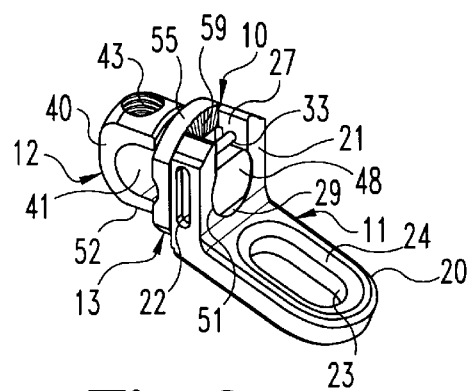
FIG. 3 is a top perspective view of the lateral connector assembly of FIGS. 1-2.
Figure 2:
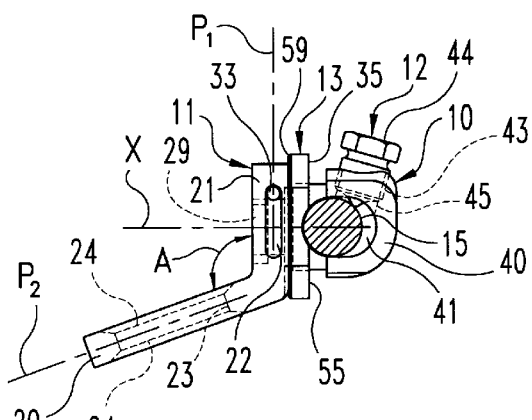
FIG. 2 is a side elevational view of the lateral connector assembly of FIG. 1.

In a further aspect of the yoke portion 21, a bore 30 is defined between the arms of the yoke portion and spanning the hub opening 27. The bore 30 is configured to receive a pin 33 that is press-fit into the bore 30 across the hub opening 27, as shown in FIGS. 1–3. The pin 33 serves to prevent removal of the clamp 12 from the lateral connector 11, once a portion of the clamp is situated within the hub opening 27 and recess 29.

The lateral connector assembly 10 also includes variable angle means 13 between the lateral connector 11 and the clamp 12. In one specific embodiment, the variable angle means 13 includes a splined face 35 (FIGS. 1 and 2; see also FIG. 11) defined on the yoke portion 21 on the surface opposite the surface including the recess 29. In other words, the splined face 35 of the yoke portion 21 is directed to face the spinal rod 15 when the lateral connector assembly 10 is in its operative position.

The clamp 12 of the lateral connector assembly 10 includes a clamp body 40 that defines a rod channel 41 therethrough. In the illustrated embodiment, the clamp 12 can be in the form of the top-tightening T-bolt provided with the Sofamor Danek TSRH® Spinal System, such as the T-bolt sold under catalog no. 828-193. Details of the top-tightening T-bolt can also be found in U.S. Pat. No. 5,282,801, assigned to Danek Medical, which disclosure is incorporated herein by reference. In this embodiment, the rod channel 41 is preferably elongated and is intersected by a threaded aperture 43. A set screw 44 is threaded into the aperture 43 so that its tip 45 engages the spinal rod 15 disposed within the rod channel 41. As the set screw 44 is threaded further into the aperture 43, the set screw tip 45 bears against the rod 15 pushing it toward the lateral connector 11 of the lateral connector assembly 10.

Figure 5:
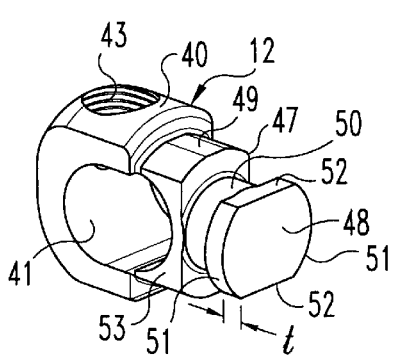
FIG. 5 is a top perspective view of a clamp component of the lateral connector assembly shown in FIGS. 1-3.

Referring to FIG. 5, details of the clamp 12 are depicted. The clamp further includes a hub 47 projecting from the clamp body 40. Preferably, the hub 47 is collinear with the longitudinal axis of the rod channel 41. The hub 47 includes an enlarged portion 48 at its terminal end and an intermediate portion 49 directly attached to the clamp body 40. In the specific embodiment, the intermediate portion 49 defines part of the rod channel 41. A post 50 separates the enlarged portion 48 and intermediate portion 49.

Figure 4:
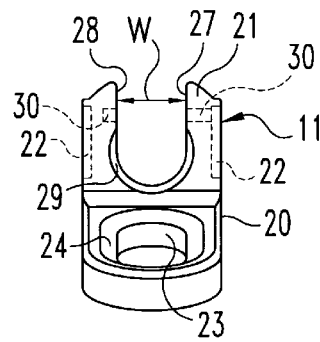
FIG. 4 is an end elevational view of the lateral connector component of the lateral connector assembly shown in FIGS. 1-3.

In accordance with the preferred embodiment, the post 50 is cylindrical and has a diameter that is less than the width W of the hub opening 27 in the lateral connector 11 (see FIG. 4). The enlarged portion 48 of the hub 47 has opposite rounded edges 51 that are preferably formed at the same diameter as the recess 29 in the yoke portion 21 of the lateral connector 11. The enlarged portion 48 also preferably includes opposite flat edges 52 disposed between the rounded edges 51. In the specific embodiment, the enlarged portion 48 has a width between its flat edges 52 that is slightly less than the width W of the hub opening 27 in the lateral connector. This permits placement of the hub 47 of the clamp 12 within the hub opening 27 either through the opening 28, or directly into the hub opening by rotating the enlarged portion 48 so that its flat edges 52 can negotiate the width of the hub opening 27. In this latter case, once the enlarged portion 48 is extended through the hub opening 27, the lateral connector 11 and clamp 12 can be rotated relative to each other so that the rounded edges 41 of the enlarged portion 48 span the hub opening, to thereby prevent removal of the enlarged portion through the hub opening 27.

In accordance with a further aspect of the invention, the enlarged portion 48 of the hub 47 has a thickness t that is less than or equal to the depth of the recess 29 defined in the yoke portion of the lateral connector 11. As shown in FIGS. 1–3, when the lateral connector assembly 10 is in its operative position, the enlarged portion 48 is filly contained within the recess 29 and is flush with or below the surface of the yoke portion 21. In this way, the clamp 12 will not interfere with the engagement of the lateral connector 11 to a bone engaging fastener. Once the enlarged portion 48 is seated within the recess 29, the pin 33 can be pressed into the bore 30 to prevent dislodgment of the clamp 12 from the lateral connector 11.

Figure 6:
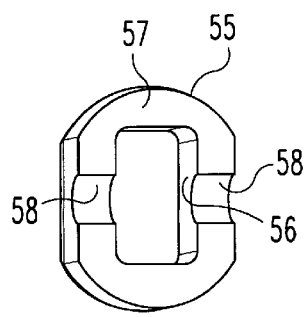
FIG. 6 is a front perspective view of a washer forming part of a variable angle means component of the lateral connector assembly shown in FIGS. 1-3.
Figure 7:
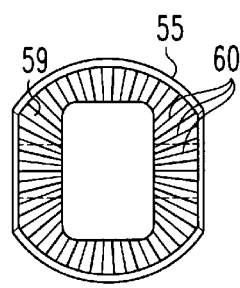
FIG. 7 is a rear elevational view of the washer shown in FIG. 6.

In the preferred embodiment, the clamp 12, and particularly the intermediate portion 49 of the hub 47, defines a generally rectangular perimeter 53. This rectangular perimeter is arranged to engage a second component of the variable angle means 13, namely washer 55, depicted in FIGS. 6-7. The washer 55 includes a substantially rectangular opening 56 that corresponds with the rectangular perimeter 53 of the clamp 12. Rather than have an entirely circular configuration, the washer has flattened sidewalls which generally correspond to the shape of the yoke portion 21 of the lateral connector 11, as depicted in FIGS. 1 and 3. The washer 55 includes a rod face 57 which is directed toward the rod, as shown in FIG. 2. The rod face 57 defines a rod groove 58 across the rectangular opening 56, which is configured to receive the rod 15 therein. Preferably, the rod groove 58 is defined at a radius that is slightly smaller than the radius of the spinal rod 15 in order to create a "three-point shear clamp" between the washer and the rod when the clamp 12 is tightened. This three-point shear clamp is a feature of the Sofamor Danek TSRH® Spinal System as implemented, for example, in the central post hooks and screws.

The opposite face of the washer 55 forms part of the variable angle means 13. Specifically, the washer includes an interdigitating face 59 that is directed against the splined face 35 of the yoke portion 21 of the lateral connector 11. This interdigitating face 59 includes a plurality of radially emanating splines 60 which correspond to similarly arranged splines on the splined face 35 of the lateral connector (see e.g. FIG. 11). The interdigitating splines between the face 59 of washer 55 and face 35 of lateral connector 11 allow the lateral connector to assume variable angular positions with respect to the washer 55. The washer 55 does not rotate with respect to the clamp 12 because the hub 47 projects into the rectangular opening 56 of the washer. Details of one specific embodiment of the variable angle means 13, together with the washer 55, can be found in U.S. Pat. No. 5,261,909, particularly FIGS. 3 and 4 and the accompanying text of that patent, and U.S. Pat. No. 5,282,801, particularly FIGS. 8-9, which disclosures are incorporated herein by reference.

In this embodiment of the present invention, the lateral connector assembly 10 provides a lateral connector 11 that allows for variable placement of a bone engaging fastener along the length of the elongated opening 23 of the connector 11. While this degree of freedom of placement of the fastener with respect to the rod is available in prior connectors, no other connector adds the additional degree of freedom of rotating the lateral connector 11 with respect to the clamp 12 and, ultimately, the rod 15. Specifically, this embodiment of the present invention permits rotation or pivoting of the lateral connector 11 with respect to an axis X that is generally coincident with a diameter of the rod 15. Thus, in circumstances where the surgeon is unable to align the bone engaging fastener to be substantially perpendicular with the rod 15, the lateral connector 11 of the assembly 10 can be rotated at the variable angle means 13 so that the elongated opening 23 is aligned with the axis of the bone engaging fastener.

In another aspect of the lateral connector assembly 10, the yoke portion 21 defines a plane $P_1$ passing transversely through the yoke portion, as depicted in FIG. 2. The plate portion 20 also defines a plane $P_2$ that passes transversely through the plate parallel to the top and bottom surfaces of the plate. In accordance with another feature of the present invention, the planes $P_1$ and $P_2$ are not perpendicular to each other, so that these planes define a plate angle A that is not at 90 degrees. Preferably, the plate angle A is at least 100 degrees and in its most preferred embodiment is 110 degrees. The plate angle A is preferably greater than 90 degrees due to the typical relative orientations of the rod and the bone engaging fastener. For example, in a pedicle fixation a bone bolt threaded into the pedicle will project poster-laterally. The rod is situated adjacent the spinous process so the lateral connector assembly engaged to the rod will be above and medial to the bone bolt. The plate portion 20 thus must angle downward, or anteriorly, and laterally outward to mate with the bone bolt, hence the preferred 110 degree angle A.

In prior lateral connectors, the lateral connector is able to be rotated about the longitudinal axis of the spinal rod 15 as necessary to orient the lateral connector with the bone engaging fastener affixed to a vertebra. However, in these prior designs, rotation of the lateral connector also requires rotation of the clamping mechanism used to fix the lateral connector to the spinal rod. In some instances, this manipulation of the lateral connector makes manipulation and activation of the clamping mechanism more cumbersome and difficult. Consequently, the present invention addresses this difficulty by providing a lateral connector, such as connector 11, in which the plate portion used to engage the bone engaging fastener is established at a non-perpendicular angle with respect to the portion of the connector engaged to the spinal rod, such as rod 15. As shown in FIG. 2, it can be seen that the elongated opening 23 of the plate portion 20 is oriented at a more optimum angle for attachment to the bone engaging fastener, while the yoke portion 21 is situated perpendicular to the axis X extending through the diameter of the rod. In this orientation, the set screw 44 of the clamp 12 is easily accessible from the top of the construct. Of course, it is understood that the clamp 12, and therefore the lateral connector 11, may still be rotated somewhat about the axis of the rod 15. However, the additional angle A provided by the lateral connector 11 means that the connector and clamp need not be rotated significantly about the rod in order to align the elongated opening 23 over a bone engaging fastener.

In some applications it may be contemplated that the plate portion 20 would need to assume a lower angle A that is less than 90 degrees. In this instance, the plane $P_2$ of FIG. 2 would be tilted upward so that the lateral connector 11 takes the form of a "V". The non-perpendicularity of the plate and yoke portions retains the features of the illustrated embodiment that make the present lateral connector assembly more versatile than prior devices.

Figure 8:
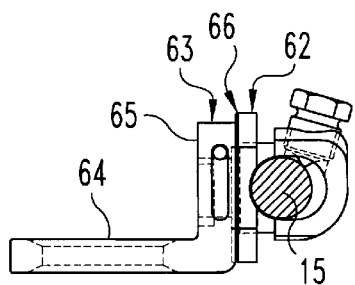
FIG. 8 is a side elevational view of a lateral connector assembly including an alternative embodiment of a lateral connector according to the present invention.

A lateral connector assembly 62 is depicted in FIG. 8, which illustrates an additional application of the variable angle attributes of the lateral connector assembly 10 shown in FIGS. 1–3. The assembly 62 includes a lateral connector 63 defined by a plate portion 64 and a yoke portion 65 that are perpendicular to each other. In this embodiment, the lateral connector 63 is capable of variable angular orientations relative to the rod 15, due to the variable angle means 66, which means is substantially identical to the variable angle means 13 described above.

Figure 10:
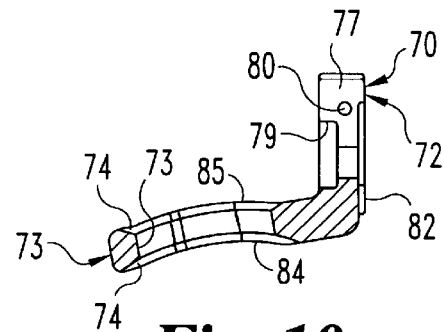
FIG. 10 is a side cross-sectional view of the lateral connector shown in FIG. 9.
Figure 9:
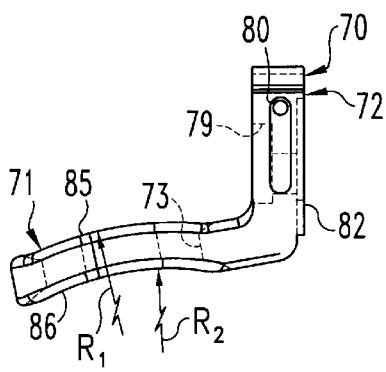
FIG. 9 is a side elevational view of a lateral connector according to a further embodiment of the present invention.
Figure 11:
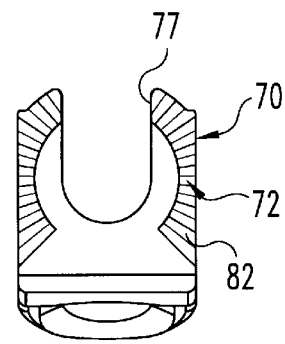
FIG. 11 is a rear elevational view of the lateral connector shown in FIGS. 9-10 illustrating a portion of a variable angle means of the lateral connector assembly.

In a further embodiment of the present invention, an lateral connector 70 is provided as shown in FIGS. 9–11. In this embodiment, the connector 70 includes a plate portion 71 and an integral yoke portion 72. The plate portion 71 defines an elongated opening 73 with a countersink 74 on the opposite surfaces of the plate portion. As shown in FIG. 11, the yoke portion 72 defines a hub opening 77 through which a clamp, such as clamp 12, can be extended. The yoke portion also defines a recess 79 (FIG. 10) that is configured to receive the enlarged portion 48 of the clamp 12. The yoke portion also defines a bore 80 extending across the hub opening 77, which is configured to receive a pin 33. The yoke portion 72 also includes a splined face 82, which constitutes part of a variable angle means, such as the means 13 of lateral connector assembly 10. The plate portion 71 and yoke portion 72 can be oriented at non-perpendicular angles relative to each other, as in the embodiment of FIGS. 1–3.

As thus far described, the lateral connector 70 is substantially similar to the lateral connector 11, and can be used in a similar manner with the clamp 12 and variable angle means 13. However, unlike the lateral connector 11, the plate portion 71 of the connector 70 of the present embodiment is curved. In particular, the plate portion 71 includes an upper surface 85 and lower surface 86, both of which are curved, the upper surface being curved at a radius $R_1$ that is greater than the radius $R_2$ of the lower surface. In this manner, then, the elongated opening 73 of the lateral connector 70 is also curved, as shown most clearly in FIG. 10.

In this embodiment, when the bone engaging fastener travels along the length of the elongated opening 73, not only does its lateral position change with respect to the rod, also its angular orientation with respect to the rod is modified. In prior lateral connectors, the bone engaging fastener is required to maintain a particular angular relationship with respect to the rod even as the fastener is located at different positions along the length of the elongated opening or slot in the connector. In some surgeries, it has been found that proper lateral positioning of the bone engaging fastener with respect to the spinal rod 15 also requires some accommodation of a variable angular orientation. In some cases, the surgeon can account for this angular orientation by pivoting the lateral connector and clamp about the spinal rod. In these cases, the detriments mentioned above arise. In order to overcome these difficulties, the lateral connector 70 of the present embodiment of the invention adds an extra degree of freedom for manipulating the connection between the lateral connector and the bone engaging fastener.

Thus, the lateral connector 70 of FIGS. 9–11 can have the following degrees of freedom: sliding movement of the connector along the length of the rod 15; rotation of the connector 70 about the longitudinal axis of the rod; lateral movement of the position of the bone engaging fastener with respect to the rod when the fastener extends through the elongated openings 73; rotation of the lateral connector 70 about the axis X extending through a diameter of the rod; and finally, variations in angular orientation of the bone engaging fastener with respect to the yoke portion 72 and rod 15 as the fastener is situated at various positions along the length of the elongated opening 74. In all, these 5 degrees of freedom for manipulation of the position of the bone engaging fastener with respect to the rod gives the surgeon the greatest possible flexibility in attaching a spinal rod, whose orientation with respect to the spine is limited, to a bone engaging fastener that is affixed to a vertebra so that its position cannot be varied.

Figure 12:
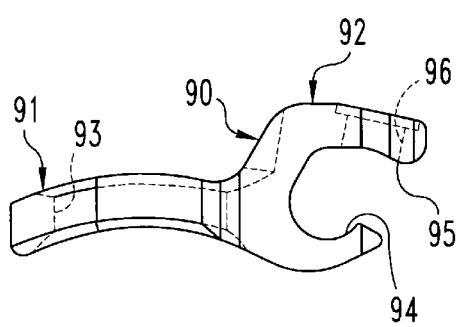
FIG. 12 is a side elevational view of an additional embodiment of a lateral connector according to the present invention.

FIG. 12 illustrates an additional embodiment of a lateral connector according to the present invention. The lateral connector 90 includes a plate portion 92, a plate portion 91 and an integral yoke portion 92. The plate portion defines an elongated slot 94, while the yoke portion 92 defines a rod channel 94 therethrough. In this embodiment, the rod channel opens into a rod slot so that the angled connector 90 can be introduced over the rod in situ. This is in contrast to the clamp 12 of the lateral connector assembly 10, which must be pre-threaded onto the spinal rod before the rod is placed within the patient. In this embodiment, the yoke portion 92 also defines a set screw bore 96 that intersects the rod channel 94. The bore 96 can receive a set screw, such as set screw 44 so that the set screw can bear directly against a spinal rod, such as rod 15, disposed within the channel 94 to fix the rod in place. In this embodiment, it can be seen that the variable angle means, such as means 13, is eliminated, thereby eliminating that degree of freedom of manipulation. However, the plate portion 91 retains the curved feature of the lateral connector 70 shown in FIG. 9.

Figure 13:
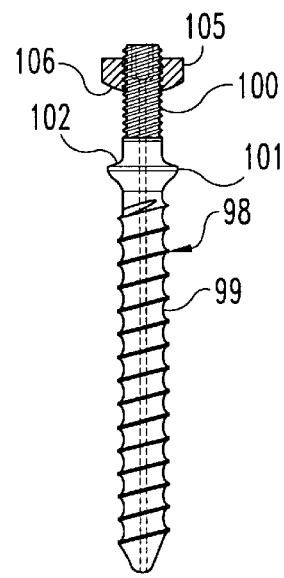
FIG. 13 is a side elevational view of a bone engaging fastener usable with the lateral connector assemblies of the present invention.

The present invention contemplates lateral connectors and connector assemblies for connecting a bone engaging fastener to a spinal rod. In accordance with the preferred embodiments of this invention, the bone engaging fastener includes a portion to project into the elongated opening, such as opening 23 of the lateral connector. In one embodiment, the bone engaging fastener can be a fastener 98 as shown in FIG. 13. In this embodiment, the fastener 98 includes bone engaging threads 99 that are configured to be threaded into the vertebral body. The bone threads 99 could also be designed for pedicle fixation, depending upon the surgical indication. The invention also contemplates that the threads 99 are replaced by a hook, such as a laminar hook configured to grasp portions of a vertebra.

The fastener 98 also includes a machine threaded portion 100 separated from the bone threads 99 by an intermediate portion 101. The intermediate portion 101 defines an arcuate shoulder 102, which is preferably configured to seat within the countersunk portion 24 of the elongated opening 23. A nut 105 is provided for threading onto the machine threaded portion 100 to clamp the fastener to the plate portion, such as portion 20 of the lateral connector. In one embodiment, the nut 105 includes a curved bottom 106 that is configured to sit within the countersink 24 at the upper surface of the plate portion 20. In a specific embodiment, the bone engaging fastener 98 can be similar to the cannulated bolts provided with the DYNA-LOK® Spinal System, such as catalog no. 843-170. The interface between the arcuate shoulder 102 and the curved bottom 106 with respective countersunk portions 24 allow some angulation, or micromotion, of the bolt 98 relative to the lateral connector 11.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed:

1. A lateral connector assembly for connecting a bone engaging fastener to an elongated member comprising:

a lateral connector having a plate portion and an integral yoke portion, said plate portion defining an elongated opening having a longitudinal axis, said opening configured to receive the bone engaging fastener therethrough at variable positions along said longitudinal axis;

a clamp having means for clamping to the elongated member; and means between said yoke portion of said lateral connector and said clamp for engaging said lateral connector to said clamp at variable angular orientations therebetween, wherein said clamp includes a body defining a channel therethrough sized to receive the elongated member therein and a hub projecting from said body and terminating in an enlarged portion, and said yoke portion defines a hub opening sized to receive said hub therethrough and having a width dimension less than a dimension of said enlarged portion of said hub.

2. The lateral connector assembly according to claim 1, wherein said means for engaging includes interdigitating locking means between said yoke portion of said lateral connector and said clamp.

3. The lateral connector assembly according to claim 2, wherein said interdigitating locking means includes mating radial splines.

4. The lateral connector assembly according to claim 3, wherein said interdigitating locking means includes a washer disposed between said yoke portion and the elongated member when the member is clamped by said clamp, said washer having a surface facing said yoke portion and defining radial splines.

5. The lateral connector assembly according to claim 4, in which the elongated member is a rod and wherein said washer includes an opposite surface facing away from said yoke portion and defining a recess for receiving a portion of the rod.

6. The lateral connector assembly according to claim 1, wherein said body defines a threaded aperture in communication with said channel and said means for clamping includes:

a set screw threadedly engaged within said aperture for pressing against the elongated member when the member is within said channel.

7. The lateral connector assembly according to claim 1, wherein said hub opening in said yoke portion is a slot open at one end and defining said width dimension.

8. The lateral connector assembly according to claim 7, wherein:

said enlarged portion of said hub has a thickness; and said yoke portion defines a recess at an end of said slot opposite said one end, said recess configured to receive said enlarged portion therein and having a depth greater than said thickness of said enlarged portion.

9. The lateral connector assembly according to claim 7, wherein said hub has a height dimension that is less than said width dimension of said slot.

10. The lateral connector assembly according to claim 7, wherein said lateral connector further defines a bore in said yoke portion across said slot and includes a pin extending through said bore and spanning said slot to prevent removal of said hub of said body through said slot.

11. The lateral connector assembly according to claim 1, wherein said means for engaging includes a washer disposed between said yoke portion and the elongated member when the member is clamped by said clamp, said washer defining a washer opening configured for sliding said washer over said hub of said body of said clamp.

12. The lateral connector assembly according to claim 11, wherein said washer opening is rectangular and said hub includes an intermediate portion having a rectangular cross-section, whereby said washer is prevented from rotating relative to said hub when said intermediate portion is within said washer opening.

13. The lateral connector assembly according to claim 11, wherein said means for engaging includes mating radial splines defined between said yoke portion of said lateral connector and said washer.

14. The lateral connector assembly according to claim 1, wherein said yoke portion defines a first plane and said plate portion of said lateral connector defines a second plane that is not substantially perpendicular to said first plane.

15. The lateral connector assembly according to claim 14, wherein said first and second planes define an angle of at least 100 degrees therebetween.

16. The lateral connector assembly according to claim 15, wherein said first and second planes define an angle of 110 degrees therebetween.

17. The lateral connector assembly according to claim 1, wherein said yoke portion defines a first plane and said plate portion of said lateral connector is curved relative to a plane substantially perpendicular to said first plane.

18. The lateral connector assembly according to claim 1, wherein said plate portion of said lateral connector includes substantially parallel opposite curved surfaces intersected by said elongated opening.

19. The lateral connector assembly according to claim 18, wherein said curved surfaces are defined at circular radii.

20. The lateral connector assembly according to claim 19, wherein said circular radii are greater than the length of said elongated opening.

21. The lateral connector assembly according to claim 1, wherein said plate portion further defines a spherical countersink adjacent said elongated opening.

* * * * *